United States Patent
Belanoff et al.

(10) Patent No.: US 6,680,310 B2
(45) Date of Patent: Jan. 20, 2004

(54) METHODS FOR PREVENTING ANTIPSYCHOTIC-INDUCED WEIGHT GAIN

(75) Inventors: Joseph K. Belanoff, Woodside, CA (US); Alan F. Schatzberg, Los Altos, CA (US)

(73) Assignee: Corcept Therapeutics, Inc., Menlo Park, CA (US)

( * ) Notice: Subject to any disclaimer, the term of this patent is extended or adjusted under 35 U.S.C. 154(b) by 0 days.

(21) Appl. No.: 10/201,356

(22) Filed: Jul. 22, 2002

(65) Prior Publication Data

US 2003/0027802 A1 Feb. 6, 2003

Related U.S. Application Data

(60) Provisional application No. 60/307,693, filed on Jul. 23, 2001.

(51) Int. Cl.$^7$ .............................................. A61K 31/56
(52) U.S. Cl. ....................... 514/179; 514/172; 514/180
(58) Field of Search ................................. 514/179, 180, 514/172

(56) References Cited

U.S. PATENT DOCUMENTS

| | | | |
|---|---|---|---|
| 5,929,058 A | 7/1999 | Deisher | |
| 6,150,349 A | 11/2000 | Schatzberg et al. | |
| 6,369,046 B1 | 4/2002 | Schatzberg et al. | |

OTHER PUBLICATIONS

Allison, D.B. et al. "Antipsychotic–induced weight gain: a comprehensive research synthesis," *Am. J. Psychiatry* Nov. 11, 1999, pp. 1686–1696, vol. 156.

Andrews, R.C. and Walker B.R. "Glucocorticoids and insulin resistance: old hormones, new targets," *Clinical Sci.* 1999, pp. 513–523, vol. 96.

Baptista, T. "Body weight gain induced by antipsychotic drugs: mechanisms and management," *Acta Psychiatr. Scand.* 1999, pp. 3–16, vol. 100.

Baptista, T. et al., "Body weight gain after administration of antipsychotic drugs: correlation with leptin, insulin and reproductive hormones," *Pharmacopsychiatry* 2000, pp.81–88, vol. 33.

Blackburn, G.L. "Weight gain and antipsychotic medication," *J. Clin. Psychiatry* 2000, pp. 36–42, vol. 61, Suppl. 8.

Friedman, J.E. et al. "Phosphoenolpyruvate carboxykinase (GTP) gene transcription and hyperglycemia are regulated by glucocorticoids in genetically obese db/db transgenic mice," *J. Biol. Chem.* Dec. 12, 1997, pp. 31475–31481, vol. 272, No. 50.

Gettys, T.W. et al. "RU–486 (mifepristone) ameliorates diabetes but does not correct deficient β–adrenergic signaling in adipocytes from mature C57BL/6J–ob/ob mice," *International J. of Obesity* 1997, pp. 865–873, vol. 21.

Green, A.I. et al. "Weight gain from novel antipsychotic drugs: need for action," *General Hospital Psychiatry* 2000, pp. 224–235, vol. 22, Harvard Mental Health Letter "Antipsychotic drugs: the weight problem," *Harvard Health Online* Dec. 2000 at <<http://www.health.harvard.edu/section.cfm?id=17>>, 4 pages total.

Melkersson, K.I. and Hulting, A.L. "Insulin and leptin levels in patients with schizophrenia or related psychoses–a comparison between different antipsychotic agents," *Psychopharm.* 2001, pp. 205–212, vol. 154.

Rigalleau, V. et al. "Diabetes as a result of atypical anti–psychotic drugs–a report of three cases," *Diabetic Med.* 2000, pp. 484–486, vol. 17.

*Primary Examiner*—Theodore J. Criares
(74) *Attorney, Agent, or Firm*—Townsend and Townsend and Crew LLP

(57) ABSTRACT

This invention generally pertains to the field of psychiatry. In particular, this invention pertains to the discovery that agents capable of inhibiting the binding of cortisol to its receptors can be used in methods for preventing antipsychotic-induced weight gain. Mifepristone, a potent specific glucocorticoid receptor antagonist, can be used in these methods. The invention also provides a kit for preventing AP-induced weight gain in a human including a glucocorticoid receptor antagonist and instructional material teaching the indications, dosage and schedule of administration of the glucocorticoid receptor antagonist.

15 Claims, No Drawings

METHODS FOR PREVENTING ANTIPSYCHOTIC-INDUCED WEIGHT GAIN

CROSS REFERENCE TO RELATED APPLICATIONS

The present application claims priority to U.S. Ser. No. 60/307,693 filed Jul. 23, 2001 herein incorporated by reference in its entirety.

FIELD OF THE INVENTION

This invention relates to the discovery that agents capable of inhibiting the biological action of the glucocorticoid receptor can be used in the methods for preventing weight gain induced by antipsychotic medications.

BACKGROUND OF THE INVENTION

Antipsychotic (AP) medications are among the most important therapeutic tools for treating various psychotic disorders. For these medications to be maximally beneficial, their adverse side effects, especially those associated with long-term administration, must be minimized. Numerous reports based on extensive clinical studies have, however, indicated that 40–80% of patients who are under chronic AP administration experience substantial weight gain, ultimately exceeding their ideal body weight by 20% or more (see, e.g., Umbricht et al., *J Clin. Psychiatry* 55 (Suppl. B):157–160, 1994; Baptista, *Acta Psychiatr. Scand.* 100:3–16, 1999). Such undesirable weight gain can significantly compromise the effectiveness of treatment for psychotic disorders. First of all, a person whose body weight significantly exceeds the healthful range is exposed to a dramatically increased risk in many serious health problems associated with obesity, such as cardiovascular disease, stroke, hypertension, type II diabetes, and certain types of cancer. Secondly, unwanted weight gain is one of the most common reasons for a patient's non-compliance of AP administration schedule, which necessarily leads to the failure of the treatment for the psychotic disorder.

The degree of weight gain induced by different AP medications varies. The newer, or atypical, AP drugs, such as clozapine and olanzapine, have shown greater ability to induce weight gain (Allison et al., *Am. J Psychiatry* 156:1686–1696, 1999). Although studies have suggested that insulin, leptin, and certain reproductive hormones play important roles in the process, the precise mechanism of AP-induced weight gain remains to be fully understood as it is believed to involve multiple factors and intricate interactions amongst them.

Insulin is synthesized and secreted by the pancreatic β-cells in response to, among other things, elevated blood glucose concentration. Acting through cell surface receptors, insulin stimulates cellular glucose uptake and may cause body weight fluctuation though a direct effect on adipose tissue and through affecting appetite via hypoglycemia (Melkersson & Hulting, *Psychopharmacology* 154:205–212, 2001). Leptin is another important hormone in body weight regulation. Encoded by the ob gene, leptin is primarily produced by adipose tissue, its circulating level positively correlating with body fat percentage and basal level of insulin. Together, leptin and insulin integrate the long-term homeostasis of body fat storage with lipid and carbohydrate metabolism (Baptista et al., *Pharmacopsychiatry* 33:81–88, 2000).

Glucocorticoid hormones are synthesized in the adrenal cortex under the control of the hypothalamic-pituitary-adrenal axis. An important element in responsiveness to many physical and psychological stresses, they are pivotal in regulating salt and water metabolism, blood pressure, immune functions, and metabolism. Cortisol is the main glucocorticoid hormone in humans. Its deficiency (Addison's disease or hypopituitarism) has been linked to postural hypotension, weight loss, and hypoglycemia, while its excess (Cushing's syndrome) has been linked to hypertension, obesity, and glucose intolerance. Cortisol's effects are, at least in part, dependent upon its antagonism of the actions of insulin, i.e., by inducing a state of insulin resistance (Andrews & Walker, *Clin. Sci.* 96:513–523, 1999).

Researchers have reported in patients under long term AP administration hormonal abnormalities, which include elevated levels of insulin and leptin, as well as altered levels of reproductive hormones in both genders (see, e.g., Baptista et al., *Pharmacopsychiatry* 33:81–88, 2000; Melkersson & Hulting, *Psychopharmacology* 154:205–212, 2001). These studies, however, have yet to establish any clear and consistent correlation between AP-induced weight gain and levels of particular hormones, such as insulin and cortisol. Hence, there has been no evidence prior to this invention that a glucocorticoid receptor antagonist can be an effective agent to prevent or reverse weight gain induced by AP medications, especially in patients having cortisol levels that fall within a normal range. Many of the actions of cortisol are mediated by binding to the type I (mineralocorticoid) receptor, which is preferentially occupied, relative to the type II (glucocorticoid) receptor, at physiological cortisol levels. As cortisol levels increase, more glucocorticoid receptors are occupied and activated. Because cortisol plays an essential role in metabolism, inhibition of all cortisol-mediated activities, however, would be fatal. Therefore, antagonists that specifically prevent type II glucocorticoid receptor functions, but do not antagonize type I mineralocorticoid receptor functions are of particular use in this invention. RU486 and similar antagonists are examples of this category of receptor antagonists.

The present inventors have determined that glucocorticoid receptor antagonists such as RU486 are effective agents for preventing or reversing AP-induced weight gain in patients with normal, increased, or decreased cortisol levels. The present invention therefore fulfills the need for an effective preventive measure for the undesirable weight gain caused by AP medications by providing methods of administering glucocorticoid receptor antagonists to patients under a long-term AP regimen.

SUMMARY OF THE INVENTION

The invention provides a method of inhibiting or reversing weight gain induced by AP medications in a patient. The method comprises administration of a therapeutically effective amount of a glucocorticoid receptor antagonist to the patient, with the proviso that the patient be not otherwise in need of treatment of with a glucocorticoid receptor antagonist and that the patient be not suffering from psychotic major depression.

In one embodiment of the invention, the methods of inhibiting or reversing AP-induced weight gain are practiced on a patient being treated with an atypical antipsychotic medication.

In another embodiment of the invention, the methods of inhibiting or reversing AP-induced weight gain are practiced on a patient being treated with an antipsychotic medication selected from the group consisting of clozapine, olanzapine, risperidone, quetiapine, and sertindole.

In another embodiment of the invention, a glucocorticoid receptor antagonist is administered to a patient who has gained at least 2 kg of weight over a ten-week period of treatment with the antipsychotic medication.

In another embodiment of the invention, a glucocorticoid receptor antagonist is administered to a patient who is at least 20% above the healthful weight range.

In another embodiment of the invention, the glucocorticoid receptor antagonist comprises a steroidal skeleton with at least one phenyl-containing moiety in the 11-beta position of the steroidal skeleton. The phenyl-containing moiety in the 11-beta position of the steroidal skeleton can be a dimethylaminophenyl moiety. In alternative embodiments, the glucocorticoid receptor antagonist comprises mifepristone, or, the glucocorticoid receptor antagonist is selected from the group consisting of RU009 and RU044.

In other embodiments, the glucocorticoid receptor antagonist is administered in a daily amount of between about 0.5 to about 20 mg per kilogram of body weight per day; between about 1 to about 10 mg per kilogram of body weight per day; or between about 1 to about 4 mg per kilogram of body weight per day. The administration can be once per day. In alternative embodiments, the mode of glucocorticoid receptor antagonist administration is oral, or by a transdermal application, by a nebulized suspension, or by an aerosol spray.

The invention also provides a kit for inhibiting or reversing AP-induced weight gain in a human, the kit comprising a glucocorticoid receptor antagonist; and, an instructional material teaching the indications, dosage and schedule of administration of the glucocorticoid receptor antagonist. In alternative embodiments, the instructional material indicates that the glucocorticoid receptor antagonist can be administered in a daily amount of about 0.5 to about 20 mg per kilogram of body weight per day, of about 1 to about 10 mg per kilogram of body weight per day, or about 1 to about 4 mg per kilogram of body weight per day. The instructional material can indicate that cortisol contributes to weight gain in patients under AP administration, and that the glucocorticoid receptor antagonist can be used to prevent or reverse such weight gain. In one embodiment, the glucocorticoid receptor antagonist in the kit is mifepristone. The mifepristone can in tablet form.

A further understanding of the nature and advantages of the present invention is realized by reference to the remaining portions of the specification and claims.

All publications, patents and patent applications cited herein are hereby expressly incorporated by reference for all purposes.

DEFINITIONS

The term "inhibiting" refers to any indicia of success in the prevention or reduction of weight gain in a patient induced by an AP medication. The prevention or reduction of AP-induced weight gain can be measured based on objective parameters, such as the results of a physical examination. For example, the methods of the invention successfully inhibit a patient's AP-induced weight gain by limiting the weight gain to no greater than 1 kg over a ten-week period of treatment with an AP medication.

The term "reversing" refers to any indicia of success in causing the loss of AP-induced weight gain already established prior to the administration of a glucocorticoid receptor antagonist. The reduction of weight already gained can be measured based on objective parameters, such as the results of a physical examination. For example, the methods of the invention successfully reverse a patient's AP-induced weight gain by causing the loss of no less than 50% of the weight gained after the start of an AP medication but before the glucocorticoid receptor antagonist administration.

The term "antipsychotic medication" refers to an agent that is capable of ameliorating a psychotic disorder in the broadest sense and functions with acceptable safety and practicality. The amelioration of symptoms can be measured both by objective and subjective standards. An antipsychotic medication may be any one agent or its derivative, or a combination of more than one agent or its derivative from tricyclic phenothiazines, thioxanthenes, and dibenzepines, as well as buytrophenones and congeners, other heterocyclics, and experimental benzamides. Its actions may depend upon the interaction with D1 or D2 dopaminergic, 5-HT$_2$ serotonergic, α-adrenergic receptors, or any other dopaminergic receptors yet to be identified. For example, chlorprothixene, clozapine, haloperidol, loxapine, mesoridazine/thioridazine, molindone, olanzapine, perphenazine, pimozide, prochlorperazine, quetiapine, risperidone, sertindole, thiothixene, trifluoperazine, ziprasidone, and zuclopenthixol are antipsychotic medications.

The term "psychotic major depression," also referred to as "psychotic depression" (Schatzberg, *Am. J. Psychiatry* 149:733–745, 1992), "psychotic (delusional) depression" (Ibid.), "delusional depression" (Glassman, *Arch. Gen. Psychiatry* 38:424–427, 1981), and "major depression with psychotic features" (see American Psychiatric Association, *Diagnostic and Statistical manual of Mental Disorders* (*DSM*), Third Edition), refers to a distinct psychiatric disorder which includes both depressive and psychotic features. Individuals manifesting both depression and psychosis, i.e., psychotic depression, are herein referred to as "psychotic depressives." It has been long-recognized in the art as a distinct syndrome, as described, for example, by Schatzberg, supra, 1992. Illustrative of this distinctiveness are studies which have found significant differences between patients with psychotic and nonpsychotic depression in glucocorticoid activity, dopamine—hydroxylase activity, levels of dopamine and serotonin metabolites, sleep measures and ventricle to brain ratios. Psychotic depressives respond very differently to treatment compared to individuals with other forms of depression, such as "non-psychotic major depression." Psychotic depressives are markedly unresponsive to tricyclics (anti-depressive) drug therapy (Glassman et al., *Am. J. Psychiatry* 1332:716–719, 1975). While psychotic depressives can respond to electroconvulsive therapy (ECT), their response time is relatively slow and the ECT has a high level of related morbidity. Clinical manifestations and diagnostic parameters of "psychotic major depression" is described in detail in *DSM* (Fourth Edition, 1995).

The term "atypical" refers to the characteristics of a newer class of antipsychotic agents that do not have the extrapyramidal side effects associated with traditional antipsychotic medications. For example, clozapine and olanzapine are atypical antipsychotic drugs.

The term "healthful weight range" refers to a body mass index (BMI) between 19 and 25, as defined by the first Federal guidelines on the identification, evaluation, and treatment of overweight and obesity developed by the National Heart, Lung, and Blood Institute, in cooperation with the National Institute of Diabetes and Digestive and Kidney Diseases (*Clinical Guidelines on the Identification, Evaluation, and Treatment of Overweight and Obesity in Adults: Evidence Report,* 1998).

The term "cortisol" refers to a family of compositions also referred to as hydrocortisone, and any synthetic or natural analogues thereof.

The term "glucocorticoid receptor" ("GR") refers to a family of intracellular receptors also referred to as the cortisol receptor, which specifically bind to cortisol and/or cortisol analogs. The term includes isoforms of GR, recombinant GR and mutated GR.

The term "mifepristone" refers to a family of compositions also referred to as RU486, or RU38.486, or 17-beta-hydroxy-11-beta-(4-dimethyl-aminophenyl)-17-alpha(1-propynyl)-estra-4,9-dien-3-one), or 11-beta-(4dimethylaminophenyl)-17-beta-hydroxy-17-alpha-(1-propynyl)-estra-4,9-dien-3-one), or analogs thereof, which bind to the GR, typically with high affinity, and inhibit the biological effects initiated/mediated by the binding of any cortisol or cortisol analogue to a GR receptor. Chemical names for RU-486 vary; for example, RU486 has also been termed:11B-[p-(Dimethylamino)phenyl]-17B-hydroxy-17-(1-propynyl)-estra-4,9-dien-3-one; 11B-(4-dimethyl-aminophenyl)-17B-hydroxy-17A-(prop-1-ynyl)-estra-4,9-dien-3-one; 17B-hydroxy-11B-(4-dimethylaminophenyl-1)-17A-(propynyl-1)-estra-4,9-diene-3-one; 17B-hydroxy-11B-(4-dimethylaminophenyl-1)-17A-(propynyl-1)-E; (11B,17B)-11-[4-dimethylamino)-phenyl]-17-hydroxy-17-(1-propynyl)estra-4,9-dien-3-one; and 11B-[4-(N,N-dimethylamino) phenyl]-17A-(prop-1-ynyl)-D-4,9-estradiene-17B-ol-3-one.

The term "specific glucocorticoid receptor antagonist" refers to any composition or compound which partially or completely inhibits (antagonizes) the binding of a glucocorticoid receptor (GR) agonist, such as cortisol, or cortisol analogs, synthetic or natural, to a GR. A "specific glucocorticoid receptor antagonist" also refers to any composition or compound which inhibits any biological response associated with the binding of a GR to an agonist. By "specific", we intend the drug to preferentially bind to the GR rather than the mineralocorticoid receptor (MR) with an affinity at least 100-fold, and frequently 1000-fold.

A patient "not otherwise in need of treatment with a glucocorticoid receptor antagonist" is a patient who is not suffering from a condition which is known in the art to be effectively treatable with glucocorticoid receptor antagonists. Conditions known in the art to be effectively treatable with glucocorticoid receptor antagonists include Cushing's disease, drug withdrawal, psychosis, dementia, stress disorders, and psychotic major depression.

DETAILED DESCRIPTION OF THE INVENTION

This invention pertains to the surprising discovery that agents capable of inhibiting glucocorticoid-induced biological responses are effective for preventing AP-induced weight gain. In patients who are to begin long term AP administration, or who have already been under long term AP administration and gained substantial weight as a result, the methods of the invention can preferably inhibit or reverse AP-induced weight gain. In one embodiment, the methods of the invention use agents that act as GR antagonists, to prevent or reverse weight gain caused by AP medications. The methods of the invention are effective in preventing AP-induced weight gain in a patient afflicted with either normal, increased or decreased levels of cortisol or other glucocorticoids, natural or synthetic.

Cortisol acts by binding to an intracellular, glucocorticoid receptor (GR). In humans, glucocorticoid receptors are present in two forms: a ligand-binding GR-alpha of 777 amino acids; and, a GR-beta isoform that differs in only the last fifteen amino acids. The two types of GR have high affinity for their specific ligands, and are considered to function through the same signal transduction pathways.

The biologic effects of cortisol, including pathologies or dysfunctions caused by hypercortisolemia, can be modulated and controlled at the GR level using receptor antagonists. Several different classes of agents are able to act as GR antagonists, i.e., to block the physiologic effects of GR-agonist binding (the natural agonist is cortisol). These antagonists include compositions, which, by binding to GR, block the ability of an agonist to effectively bind to and/or activate the GR. One family of known GR antagonists, mifepristone and related compounds, are effective and potent anti-glucocorticoid agents in humans (Bertagna, *J. Clin. Endocrinol. Metab.* 59:25, 1984). Mifepristone binds to the GR with high affinity, with a K of dissociation $<10^{-9}$ M (Cadepond, *Annu. Rev. Med.* 48:129, 1997). Thus, in one embodiment of the invention, mifepristone and related compounds are used to prevent weight gain induced by AP medications.

AP-induced weight gain can be easily detected by regular physical examinations. Thus, a variety of means of monitoring body weight change and assessing the success of weight management by the methods of the invention, i.e., the success and extent to which AP-induced weight gain is inhibited or reversed, can be used, and a few exemplary means are set forth herein. These means can include simple body weight measurement and sophisticated methods of determining body fat percentage as described below.

As the methods of the invention include use of any means to inhibit the biological effects of an agonist-bound GR, illustrative compounds and compositions which can be used to treat delirium are also set forth. Routine procedures that can be used to identify further compounds and compositions able to block the biological response caused by a GR-agonist interaction for use in practicing the methods of the invention are also described. As the invention provides for administering these compounds and compositions as pharmaceuticals, routine means to determine GR antagonist drug regimens and formulations to practice the methods of the invention are set forth below.

1. Determination of AP-Induced Weight Gain

Weight gain as a result of prolonged AP treatment is determined primarily based on comparison of a patient's body weight before and after the administration. The weight gained may also be reflected in increased body fat percentage. To be considered to have gained weight as a result of AP treatment, a patient should become at least 2 kg heavier after being placed on an AP regimen for a ten-week period. In some embodiments of the invention, the patient's weight gain is greater, e.g., at least 3, 4, 5, 10, 15, or 20 kg, over a ten-week period of AP treatment. Weight gain may also be measured by a percentage increase in weight during AP administration, e.g., an increase of body weight by at least 5%, 10%, 15%, or 20%, over a ten-week period of AP treatment. An increase in body fat percentage may also be used to measure weight gain, e.g., an increase of body fat percentage by at least 2%, 5%, 10%, or 15% over a ten-week period of AP treatment.

AP-induced weight gain may be determined and evaluated with any one of several objective, standard instruments known in the art, which include scales and instruments that measure body fat percentage. The simple instrument of a scale is routinely used by all professional health care practitioners. More sophisticated instruments to measure body fat percentage operate based on skin-fold methodology and measurement of body density or electrical resistance.

2. General Laboratory Procedures

When practicing the methods of the invention, a number of general laboratory tests can be used to assist in the progress of the patient under AP administration, including monitoring of parameters such as blood cortisol, drug metabolism, etc. These procedures can be helpful because all patients metabolize and react to drugs uniquely. In addition, such monitoring may be important because each GR antagonist has different pharmacokinetics. Different patients and AP medications may require different dosage regimens and formulations. Such procedures and means to determine dosage regimens and formulations are well described in the scientific and patent literature. A few illustrative examples are set forth below.

a. Determining Blood Cortisol Levels

Varying levels of blood cortisol have been associated with AP-induced weight gain, although the invention may also be practiced upon patients with apparently normal levels of blood cortisol. Thus, monitoring blood cortisol and determining baseline cortisol levels are useful laboratory tests to aid in preventing weight gain induced by AP medications. A wide variety of laboratory tests exist that can be used to determine whether an individual is normal, hypo- or hyper-cortisolemic. Patients who are to receive or have been receiving long term AP treatment typically have normal levels of cortisol that are often less than 25 $\mu$g/dl in the morning, and frequently about 15 $\mu$g/dl or less in the afternoon, although the values often fall at the high end of the normal range, which is generally considered to be 5–15 $\mu$g/dl in the afternoon.

Immunoassays such as radioimmunoassays are commonly used because they are accurate, easy to do and relatively cheap. Because levels of circulating cortisol are an indicator of adrenocortical function, a variety of stimulation and suppression tests, such as ACTH Stimulation, ACTH Reserve, or dexamethasone suppression (see, e.g., Greenwald, *Am. J. Psychiatry* 143:442–446, 1986), can also provide diagnostic, prognostic or other information to be used adjunctively in the methods of the invention.

One such assay available in kit form is the radioimmunoassay available as "Double Antibody Cortisol Kit" (Diagnostic Products Corporation, Los Angeles, Calif.), (*Acta Psychiatr. Scand.* 70:239–247, 1984). This test is a competitive radioimmunoassay in which $^{125}$I-labeled cortisol competes with cortisol from an clinical sample for antibody sites. In this test, due to the specificity of the antibody and lack of any significant protein effect, serum and plasma samples require neither preextraction nor predilution. This assay is described in further detail in Example 2, below.

b. Determination of Blood/Urine Mifepristone Levels

Because a patient's metabolism, clearance rate, toxicity levels, etc. differs with variations in underlying primary or secondary disease conditions, drug history, age, general medical condition and the like, it may be necessary to measure blood and urine levels of GR antagonist. Means for such monitoring are well described in the scientific and patent literature. As in one embodiment of the invention mifepristone is administered to prevent AP-induced weight gain, an illustrative example of determining blood and urine mifepristone levels is set forth in the Example below.

c. Other Laboratory Procedures

Because the mechanism of AP-induced weight gain may be complex, a number of additional laboratory tests can be used adjunctively in the methods of the invention to assist in diagnosis, treatment efficacy, prognosis, toxicity and the like. For example, diagnosis and treatment assessment can be augmented by monitoring and measuring glucocorticoid-sensitive variables, including but limited to fasting blood sugar, blood sugar after oral glucose administration, plasma concentrations thyroid stimulating hormone (TSH), corticosteroid-binding globulin, luteinizing hormone (LH), testosterone-estradiol-binding globulin, leptin, insulin, and/or total and free testosterone.

Laboratory tests monitoring and measuring GR antagonist metabolite generation, plasma concentrations and clearance rates, including urine concentration of antagonist and metabolites, may also be useful in practicing the methods of the invention. For example, mifepristone has two hydrophilic, N-monomethylated and N-dimethylated, metabolites. Plasma and urine concentrations of these metabolites (in addition to RU486) can be determined using, for example, thin layer chromatography, as described in Kawai *Pharmacol. and Experimental Therapeutics* 241:401–406, 1987.

3. Glucocorticoid Receptor Antagonists to Inhibit or Reverse AP-Induced Weight Gain The invention provides for methods of inhibiting or reversing weight gain induced by AP medications utilizing any composition or compound that can block a biological response associated with the binding of cortisol or a cortisol analogue to a GR. Antagonists of GR activity utilized in the methods of the invention are well described in the scientific and patent literature. A few illustrative examples are set forth below.

a. Steroidal Anti-Glucocorticoids as GR Antagonists.

Steroidal glucocorticoid antagonists are administered to inhibit or reverse AP-induced weight gain in various embodiments of the invention. Steroidal antiglucocorticoids can be obtained by modification of the basic structure of glucocorticoid agonists, i.e., varied forms of the steroid backbone. The structure of cortisol can be modified in a variety of ways. The two most commonly known classes of structural modifications of the cortisol steroid backbone to create glucocorticoid antagonists include modifications of the 11-beta hydroxy group and modification of the 17-beta side chain (see, e.g., Lefebvre, *J. Steroid Biochem.* 33:557–563, 1989).

Examples of steroidal GR antagonists include androgen-type steroid compounds as described in U.S. Pat. No. 5,929,058, and the compounds disclosed in U.S. Pat. Nos. 4,296,206; 4,386,085; 4,447,424; 4,477,445; 4,519,946; 4,540,686; 4,547,493; 4,634,695; 4,634,696; 4,753,932; 4,774,236; 4,808,710; 4,814,327; 4,829,060; 4,861,763; 4,912,097; 4,921,638; 4,943,566; 4,954,490; 4,978,657; 5,006,518; 5,043,332; 5,064,822; 5,073,548; 5,089,488; 5,089,635; 5,093,507; 5,095,010; 5,095,129; 5,132,299; 5,166,146; 5,166,199; 5,173,405; 5,276,023; 5,380,839; 5,348,729; 5,426,102; 5,439,913; 5,616,458, and 5,696,127. Such steroidal GR antagonists include cortexolone, dexamethasone-oxetanone, 19-nordeoxycorticosterone, 19-norprogesterone, cortisol-21-mesylate; dexamethasone-21-mesylate, 11$\beta$-(4-dimethylaminoethoxyphenyl)-17$\alpha$-propynyl-17$\beta$-hydroxy-4,9-estradien-3-one (RU009), and 17$\beta$-hydroxy-17$\alpha$-19-(4-methylphenyl)androsta-4,9(11)-dien-3-one (RU044).

i) Removal or Substitution of the 11-beta Hydroxy Group

Glucocorticoid agonists with modified steroidal backbones comprising removal or substitution of the 11-beta hydroxy group are administered in one embodiment of the invention. This class includes natural antiglucocorticoids, including cortexolone, progesterone and testosterone derivatives, and synthetic compositions, such as mifepristone (Lefebvre, et al. supra). Preferred embodiments of the invention include all 11-beta-aryl steroid backbone derivatives because these compounds are devoid of progesterone receptor (PR) binding activity (Agarwal, *FEBS* 217:221–226, 1987). Another preferred embodiment comprises an 11-beta phenyl-aminodimethyl steroid backbone derivative, i.e., mifepristone, which is both an effective anti-glucocorticoid and anti-progesterone agent. These compositions act as reversibly-binding steroid receptor antagonists. For example, when bound to a 11-beta phenyl-aminodimethyl steroid, the steroid receptor is maintained in a conformation that cannot bind its natural ligand, such as cortisol in the case of GR (Cadepond, 1997, supra).

Synthetic 11-beta phenyl-aminodimethyl steroids include mifepristone, also known as RU486, or 17-beta-hydrox-11-beta-(4-dimethyl-aminophenyl)17-alpha-(1-propynyl)estra-4,9-dien-3-one). Mifepristone has been shown to be a powerful antagonist of both the progesterone and glucocorticoid (GR) receptors. Another 11-beta phenyl-aminodimethyl steroids shown to have GR antagonist effects includes RU009 (RU39.009), 11-beta-(4-dimethyl-aminoethoxyphenyl)-17-alpha-(propynyl-17 beta-hydroxy-4,9-estradien-3-one) (see Bocquel, *J. Steroid Biochem. Molec. Biol.* 45:205–215, 1993). Another GR antagonist related to RU486 is RU044 (RU43.044) 17-beta-hydrox-17-alpha-19-(4-methyl-phenyl)-androsta-4,9 (11)-dien-3-one))Bocquel, 1993, supra). See also Teutsch, *Steroids* 38:651–665, 1981; U.S. Pat. Nos. 4,386,085 and 4,912,097.

One embodiment includes compositions containing the basic glucocorticoid steroid structure which are irreversible anti-glucocorticoids. Such compounds include alpha-keto-methanesulfonate derivatives of cortisol, including cortisol-21-mesylate (4-pregnene-11-beta, 17-alpha, 21-triol-3, 20-dione-21-methane-sulfonate and dexamethasone-21-mesylate (16-methyl-9 alpha-fluoro-1,4-pregnadiene-11 beta, 17-alpha, 21-triol-3, 20-dione-21-methane-sulfonate). See Simons, *J. Steroid Biochem.* 24:25–32, 1986; Mercier, *J. Steroid Biochem.* 25:11–20, 1986; U.S. Pat. No. 4,296,206.

ii) Modification of the 17-beta Side Chain Group

Steroidal antiglucocorticoids which can be obtained by various structural modifications of the 17-beta side chain are also used in the methods of the invention. This class includes synthetic antiglucocorticoids such as dexamethasone-oxetanone, various 17, 21-acetonide derivatives and 17-beta-carboxamide derivatives of dexamethasone (Lefebvre, 1989, supra; Rousseau, *Nature* 279:158–160, 1979).

iii) Other Steroid Backbone Modifications

GR antagonists used in the various embodiments of the invention include any steroid backbone modification which effects a biological response resulting from a GR-agonist interaction. Steroid backbone antagonists can be any natural or synthetic variation of cortisol, such as adrenal steroids missing the C-19 methyl group, such as 19-nordeoxycorticosterone and 19-norprogesterone (Wynne, *Endocrinology* 107:1278–1280, 1980).

In general, the 11-beta side chain substituent, and particularly the size of that substituent, can play a key role in determining the extent of a steroid's antiglucocorticoid activity. Substitutions in the A ring of the steroid backbone can also be important. 17-hydroxypropenyl side chains generally decrease antiglucocorticoid activity in comparison to 17-propinyl side chain containing compounds.

Additional glucocorticoid receptor antagonists known in the art and suitable for practice of the invention include 21-hydroxy-6,19-oxidoprogesterone (see Vicent, *Mol. Pharm.* 52:749–753, 1997), (6β, 11β, 17β)-11-(4-dimethyl-aminophenyl)-6 methyl-4', 5'-dihydro [estra-4, 9-diene-17, 2' (3H')-furan]-3-one ("Org 31710", see Mizutani, *J Steroid Biochem Mol Biol* 42(7):695–704, 1992), Org31806, Org34517, RU43044, (17-beta-hydroxy-11-beta-/4-/[methyl]-[1-methylehtyl]aminophenyl/-17alpha-[prop-1-ynyl]estra-4–9-diene-3-one ("RU40555", see Kim, *J Steroid Biochem Mol Biol.* 67(3):213–22, 1998), RU28362, and ZK98299.

b. Non-Steroidal Anti-Glucocorticoids as Antagonists.

Non-steroidal glucocorticoid antagonists are also used in the methods of the invention to inhibit or reverse AP-induced weight gain. These include synthetic mimetics and analogs of proteins, including partially peptidic, pseudopeptidic and non-peptidic molecular entities. For example, oligomeric peptidomimetics useful in the invention include (alpha-beta-unsaturated) peptidosulfonamides, N-substituted glycine derivatives, oligo carbamates, oligo urea peptidomimetics, hydrazinopeptides, oligosulfones and the like (see, e.g., Amour, *Int. J. Pept. Protein Res.* 43:297–304, 1994; de Bont, *Bioorganic & Medicinal Chem.* 4:667–672, 1996). The creation and simultaneous screening of large libraries of synthetic molecules can be carried out using well-known techniques in combinatorial chemistry, for example, see van Breemen, *Anal Chem* 69:2159–2164, 1997; and Lam, *Anticancer Drug Des* 12:145–167, 1997. Design of peptidomimetics specific for GR can be designed using computer programs in conjunction with combinatorial chemistry (combinatorial library) screening approaches (Murray, *J. of Computer-Aided Molec. Design* 9:381–395, 1995; Bohm, *J. of Computer-Aided Molec. Design* 10:265–272, 1996). Such "rational drug design" can help develop peptide isomerics and conformers including cycloisomers, retro-inverso isomers, retro isomers and the like (as discussed in Chorev, *TibTech* 13:438–445, 1995).

Examples of non-steroidal GR antagonists include ketoconazole, clotrimazole; N-(triphenylmethyl)imidazole; N-([2-fluoro-9-phenyl]fluorenyl)imidazole; N-([2-pyridyl]diphenylmethyl)imidazole; N-(2-[4,4',4"-trichlorotrityl]oxyethyl)morpholine; 1-(2[4,4',4"-trichlorotrityl]oxyethyl)-4-(2-hydroxyethyl)piperazine dimaleate; N-([4,4',4"]-trichlorotrityl)imidazole; 9-(3-mercapto-1,2,4-triazolyl)-9-phenyl-2,7-difluorofluorenone; 1-(2-chlorotrityl)-3,5-dimethylpyrazole; 4-(morpholinomethyl)-A-(2-pyridyl)benzhydrol; 5-(5-methoxy-2-(N-methylcarbamoyl)-phenyl)dibenzosuberol; N-(2-chlorotrityl)-L-prolinol acetate; 1-(2-chlorotrityl)-2-methylimidazole; 1-(2-chlorotrityl)-1,2,4-triazole; 1,S-bis(4,4',4"-trichlorotrityl)-1,2,4-triazole-3-thiol; and N-((2,6-dichloro-3-methylphenyl)diphenyl)methylimidazole (see U.S. Pat. No. 6,051,573); the GR antagonist compounds disclosed in U.S. Pat. No. 5,696,127; the glucocorticoid receptor antagonists disclosed in Bradley et al., *J. Med. Chem.* 45, 2417–2424 (2002), e.g., 4a(S)-Benzyl-2(R)-chloroethynyl-1,2,3,4,4a,9,10,10a(R)-octahydro-phenanthrene-2,7-diol (CP 394531) and 4a(S)-Benzyl-2(R)-prop-1-ynyl-1,2,3,4,4a,9,10,10a(R)-octahydro-phenanthrene-2,7-diol (CP 409069); the compound ORG 34517 disclosed in Hoyberg et al., *Int'l J. of Neuro-psychopharmacology*, 5:Supp. 1, S148 (2002); the compounds disclosed in PCT International Application No. WO 96/19458, which describes non-steroidal compounds which are high-affinity, highly selective antagonists for steroid receptors, such as 6-substituted-1,2-dihydro-N-protected-quinolines; and some κ opioid ligands, such as the κ opioid compounds dynorphin-1,13-diamide, U50,488 (trans-(1R,2R)-3,4-dichloro-N-methyl-N-[2-(1-pyrrolidinyl)cyclohexyl]benzeneacetamide), bremazocine and ethylketocyclazocine; and the non-specific opioid receptor ligand, naloxone, as disclosed in Evans et al., *Endocrin.*, 141:2294–2300 (2000).

c. Identifying Specific Glucocorticoid Receptor Antagonists

Because any specific GR antagonist can be used to inhibit or reverse AP-induced weight gain in the methods of the invention, in addition to the compounds and compositions described above, additional useful GR antagonists can be determined by the skilled artisan. A variety of such routine, well-known methods can be used and are described in the scientific and patent literature. They include in vitro and in vivo assays for the identification of additional GR antagonists. A few illustrative examples are described below.

One assay that can be used to identify a GR antagonist of the invention measures the effect of a putative GR antagonist on tyrosine amino-transferase activity in accordance with the method of Granner, *Meth. Enzymol.* 15:633, 1970. This analysis is based on measurement of the activity of the liver enzyme tyrosine amino-transferase (TAT) in cultures of rat hepatoma cells (RHC). TAT catalyzes the first step in the metabolism of tyrosine and is induced by glucocorticoids (cortisol) both in liver and hepatoma cells. This activity is easily measured in cell extracts. TAT converts the amino group of tyrosine to 2-oxoglutaric acid. P-hydroxyphenylpyruvate is also formed. It can be converted to the more stable p-hydroxybenzaldehyde in an alkaline solution and quantitated by absorbance at 331 nm. The putative GR antagonist is co-administered with cortisol to whole liver, in vivo or ex vivo, or hepatoma cells or cell extracts. A compound is identified as a GR antagonist when its administration decreases the amount of induced TAT activity, as compared to control (i.e., only cortisol or GR agonist added) (see also Shirwany, *Biochem. Biophys. Acta* 886:162–168, 1986).

Further illustrative of the many assays which can be used to identify compositions utilized in the methods of the invention, in addition to the TAT assay, are assays based on glucocorticoid activities in vivo. For example, assays that assess the ability of a putative GR antagonist to inhibit uptake of $^3$H-thymidine into DNA in cells which are stimulated by glucocorticoids can be used. Alternatively, the putative GR antagonist can complete with $^3$H-dexamethasone for binding to a hepatoma tissue culture GR (see, e.g., Choi, et al., *Steroids* 57:313–318, 1992). As another example, the ability of a putative GR antagonist to block nuclear binding of $^3$H-dexamethasone-GR complex can be used (Alexandrova et al., J Steroid Biochem. Mol. Biol. 41:723–725, 1992). To further identify putative GR antagonists, kinetic assays able to discriminate between glucocorticoid agonists and antagonists by means of receptor-binding kinetics can also be used (as described in Jones, *Biochem J.* 204:721–729, 1982).

In another illustrative example, the assay described by Daune, *Molec. Pharm.* 13:948–955, 1977; and in U.S. Pat. No. 4,386,085, can be used to identify anti-glucocorticoid activity. Briefly, the thymocytes of adrenalectomized rats are incubated in nutritive medium containing dexamethasone with the test compound (the putative GR antagonist) at varying concentrations. $^3$H-uridine is added to the cell culture, which is further incubated, and the extent of incorporation of radiolabel into polynucleotide is measured. Glucocorticoid agonists decrease the amount of $^3$H-uridine incorporated. Thus, a GR antagonist will oppose this effect.

For additional compounds that can be utilized in the methods of the invention and methods of identifying and making such compounds, see U.S. Pat. Nos.: 4,296,206 (see above); 4,386,085 (see above); 4,447,424; 4,477,445; 4,519,946; 4,540,686; 4,547,493; 4,634,695; 4,634,696; 4,753,932; 4,774,236; 4,808,710; 4,814,327; 4,829,060; 4,861,763; 4,912,097; 4,921,638; 4,943,566; 4,954,490; 4,978, 657; 5,006,518; 5,043,332; 5,064,822; 5,073,548; 5,089,488; 5,089,635; 5,093,507; 5,095,010; 5,095,129; 5,132,299; 5,166,146; 5,166,199; 5,173,405; 5,276,023; 5,380,839; 5,348,729; 5,426,102; 5,439,913; and 5,616,458; and WO 96/19458, which describes non-steroidal compounds which are high-affinity, highly selective modulators (antagonists) for steroid receptors, such as 6-substituted-1, 2-dihydro N-1 protected quinolines.

The specificity of the antagonist for the GR relative to the MR can be measured using a variety of assays known to those of skill in the art. For example, specific antagonists can be identified by measuring the ability of the antagonist to bind to the GR compared to the MR (see, e.g., U.S. Pat. Nos. 5,606,021; 5,696,127; 5,215,916; 5,071,773). Such an analysis can be performed using either direct binding assay or by assessing competitive binding to the purified GR or MR in the presence of a known antagonist. In an exemplary assay, cells that are stably expressing the glucocorticoid receptor or mineralocorticoid receptor (see, e.g., U.S. Pat. 5,606,021) at high levels are used as a source of purified receptor. The affinity of the antagonist for the receptor is then directly measured. Those antagonists that exhibit at least a 100-fold higher affinity, often 1000-fold, for the GR relative to the MR are then selected for use in the methods of the invention.

A GR-specific antagonist may also be defined as a compound that has the ability to inhibit GR-mediated activities, but not MR-mediated activities. One method of identifying such a GR-specific antagonist is to assess the ability of an antagonist to prevent activation of reporter constructs using transfection assays (see, e.g., Bocquel et al, *J. Steroid Biochem Molec. Biol.* 45:205–215, 1993; U.S. Pat. Nos. 5,606,021, 5,929,058). In an exemplary transfection assay, an expression plasmid encoding the receptor and a reporter plasmid containing a reporter gene linked to receptor-specific regulatory elements are cotransfected into suitable receptor-negative host cells. The transfected host cells are then cultured in the presence and absence of a hormone, such as cortisol or analog thereof, able to activate the hormone responsive promoter/enhancer element of the reporter plasmid. Next the transfected and cultured host cells are monitored for induction (i.e., the presence) of the product of the reporter gene sequence. Finally, the expression and/or steroid binding-capacity of the hormone receptor protein (coded for by the receptor DNA sequence on the expression plasmid and produced in the transfected and cultured host cells), is measured by determining the activity of the reporter gene in the presence and absence of an antagonist. The antagonist activity of a compound may be determined in comparison to known antagonists of the GR and MR receptors (see, e.g., U.S. Pat. No. 5,696,127). Efficacy is then reported as the percent maximal response observed for each compound relative to a reference antagonist compound. A GR-specific antagonist is considered to exhibit at least a 100-fold, often 1000-fold or greater, activity towards the GR relative to the MR.

4. Inhibiting or Reversing AP-Induced Weight Gain Using Glucocorticoid Receptor Antagonists Antiglucocorticoids, such as mifepristone, are formulated as pharmaceuticals to be used in the methods of the invention to inhibit or reverse AP-induced weight gain. Any composition or compound that can block a biological response associated with the binding of cortisol or a cortisol analogue to a GR can be used as a pharmaceutical in the invention. Routine means to determine GR antagonist drug regimens and formulations to practice the methods of the invention are well described in the patent and scientific literature, and some illustrative examples are set forth below.

a. Glucocorticoid Receptor Antagonists as Pharmaceutical Compositions

The GR antagonists used in the methods of the invention can be administered by any means known in the art, e.g., parenterally, topically, orally, or by local administration, such as by aerosol or transdermally. The methods of the invention provide for prophylactic and/or therapeutic treatments. The GR antagonists as pharmaceutical formulations can be administered in a variety of unit dosage forms depending upon the condition or disease and the degree of psychosis, the general medical condition of each patient, the resulting preferred method of administration and the like. Details on techniques for formulation and administration are well described in the scientific and patent literature, see, e.g., the latest edition of Remington's Pharmaceutical Sciences, Maack Publishing Co, Easton Pa. ("Remington's"). Therapeutically effective amounts of glucocorticoid blockers suitable for practice of the method of the invention may range from about 0.5 to about 25 milligrams per kilogram (mg/kg). A person of ordinary skill in the art will be able without undue experimentation, having regard to that skill and this disclosure, to determine a therapeutically effective amount of a particular glucocorticoid blocker compound for practice of this invention.

In general, glucocorticoid blocker compounds may be administered as pharmaceutical compositions by any method known in the art for administering therapeutic drugs. Compositions may take the form of tablets, pills, capsules, semisolids, powders, sustained release formulations, solutions, suspensions, elixirs, aerosols, or any other appropriate compositions; and comprise at least one compound of this invention in combination with at least one pharmaceutically acceptable excipient. Suitable excipients are well known to persons of ordinary skill in the art, and they, and the methods of formulating the compositions, may be found in such standard references as Alfonso AR: Remington's Pharmaceutical Sciences, 17th ed., Mack Publishing Company, Easton Pa., 1985. Suitable liquid carriers, especially for injectable solutions, include water, aqueous saline solution, aqueous dextrose solution, and glycols.

Aqueous suspensions of the invention contain a GR antagonist in admixture with excipients suitable for the manufacture of aqueous suspensions. Such excipients include a suspending agent, such as sodium carboxymethylcellulose, methylcellulose, hydroxypropylmethylcellulose, sodium alginate, polyvinylpyrrolidone, gum tragacanth and gum acacia, and dispersing or wetting agents such as a naturally occurring phosphatide (e.g., lecithin), a condensation product of an alkylene oxide with a fatty acid (e.g., polyoxyethylene stearate), a condensation product of ethylene oxide with a long chain aliphatic alcohol (e.g., heptadecaethylene oxycetanol), a condensation product of ethylene oxide with a partial ester derived from a fatty acid and a hexitol (e.g., polyoxyethylene sorbitol mono-oleate), or a condensation product of ethylene oxide with a partial ester derived from fatty acid and a hexitol anhydride (e.g., polyoxyethylene sorbitan monooleate). The aqueous suspension can also contain one or more preservatives such as ethyl or n-propyl p-hydroxybenzoate, one or more coloring agents, one or more flavoring agents and one or more sweetening agents, such as sucrose, aspartame or saccharin. Formulations can be adjusted for osmolarity.

Oil suspensions can be formulated by suspending a GR antagonist in a vegetable oil, such as arachis oil, olive oil, sesame oil or coconut oil, or in a mineral oil such as liquid paraffin; or a mixture of these. The oil suspensions can contain a thickening agent, such as beeswax, hard paraffin or cetyl alcohol. Sweetening agents can be added to provide a palatable oral preparation, such as glycerol, sorbitol or sucrose. These formulations can be preserved by the addition of an antioxidant such as ascorbic acid. As an example of an injectable oil vehicle, see Minto, *J. Pharmacol. Exp. Ther.* 281:93–102, 1997. The pharmaceutical formulations of the invention can also be in the form of oil-in-water emulsions. The oily phase can be a vegetable oil or a mineral oil, described above, or a mixture of these. Suitable emulsifying agents include naturally-occurring gums, such as gum acacia and gum tragacanth, naturally occurring phosphatides, such as soybean lecithin, esters or partial esters derived from fatty acids and hexitol anhydrides, such as sorbitan mono-oleate, and condensation products of these partial esters with ethylene oxide, such as polyoxyethylene sorbitan mono-oleate. The emulsion can also contain sweetening agents and flavoring agents, as in the formulation of syrups and elixirs. Such formulations can also contain a demulcent, a preservative, or a coloring agent.

Glucocorticoid blocker pharmaceutical formulations can be prepared according to any method known to the art for the manufacture of pharmaceuticals. Such drugs can contain sweetening agents, flavoring agents, coloring agents and preserving agents. Any glucocorticoid blocker formulation can be admixtured with nontoxic pharmaceutically acceptable excipients which are suitable for manufacture.

Typically, glucocorticoid blocker compounds suitable for use in the practice of this invention will be administered orally. The amount of a compound of this invention in the composition may vary widely depending on the type of composition, size of a unit dosage, kind of excipients, and other factors well known to those of ordinary skill in the art. In general, the final composition may comprise from 0.000001 percent by weight (% w) to 10% w of the glucocorticoid blocker compounds, preferably 0.00001 % w to 1% w, with the remainder being the excipient or excipients. For example, the GR antagonist mifepristone is given orally in tablet form, with dosages in the range of between about 0.5 and 25 mg/kg, more preferably between about 0.75 mg/kg and 15 mg/kg, most preferably about 10 mg/kg.

Pharmaceutical formulations for oral administration can be formulated using pharmaceutically acceptable carriers well known in the art in dosages suitable for oral administration. Such carriers enable the pharmaceutical formulations to be formulated in unit dosage forms as tablets, pills, powder, dragees, capsules, liquids, lozenges, gels, syrups, slurries, suspensions, etc. suitable for ingestion by the patient. Pharmaceutical preparations for oral use can be obtained through combination of glucocorticoid blocker compounds with a solid excipient, optionally grinding a resulting mixture, and processing the mixture of granules, after adding suitable additional compounds, if desired, to obtain tablets or dragee cores. Suitable solid excipients are carbohydrate or protein fillers and include, but are not limited to sugars, including lactose, sucrose, mannitol, or sorbitol; starch from corn, wheat, rice, potato, or other plants; cellulose such as methyl cellulose, hydroxypropylmethyl-cellulose or sodium carboxymethyl-cellulose; and gums including arabic and tragacanth; as well as proteins such as gelatin and collagen. If desired, disintegrating or solubilizing agents may be added, such as the cross-linked polyvinyl pyrrolidone, agar, alginic acid, or a salt thereof, such as sodium alginate.

The GR antagonists of this invention can also be administered in the form of suppositories for rectal administration of the drug. These formulations can be prepared by mixing the drug with a suitable non-irritating excipient which is solid at ordinary temperatures but liquid at the rectal temperatures and will therefore melt in the rectum to release the drug. Such materials are cocoa butter and polyethylene glycols.

The GR antagonists of this invention can also be administered by in intranasal, intraocular, intravaginal, and intrarectal routes including suppositories, insufflation, powders and aerosol formulations (for examples of steroid inhalants, see Rohatagi, *J. Clin. Pharmacol.* 35:1187–1193, 1995; Tjwa, *Ann. Allergy Asthma Immunol.* 75:107–111, 1995).

The GR antagonists of the invention can be delivered by transdermally, by a topical route, formulated as applicator sticks, solutions, suspensions, emulsions, gels, creams, ointments, pastes, jellies, paints, powders, and aerosols.

The GR antagonists of the invention can also be delivered as microspheres for slow release in the body. For example, microspheres can be administered via intradermal injection of drug (e.g., mifepristone)-containing microspheres, which slowly release subcutaneously (see Rao, *J. Biomater Sci. Polym. Ed.* 7:623–645, 1995; as biodegradable and injectable gel formulations (see, e.g., Gao *Pharm. Res.* 12:857–863, 1995); or, as microspheres for oral administration (see, e.g., Eyles, *J. Pharm. Pharmacol.* 49:669–674, 1997). Both transdermal and intradermal routes afford constant delivery for weeks or months.

The GR antagonist pharmaceutical formulations of the invention can be provided as a salt and can be formed with many acids, including but not limited to hydrochloric, sulfuric, acetic, lactic, tartaric, malic, succinic, etc. Salts tend to be more soluble in aqueous or other protonic solvents that are the corresponding free base forms. In other cases, the preferred preparation may be a lyophilized powder in 1 mM–50 mM histidine, 0.1%–2% sucrose, 2%–7% mannitol at a pH range of 4.5 to 5.5, that is combined with buffer prior to use.

In another embodiment, the GR antagonist formulations of the invention are useful for parenteral administration, such as intravenous (IV) administration. The formulations for administration will commonly comprise a solution of the GR antagonist (e.g., mifepristone) dissolved in a pharmaceutically acceptable carrier. Among the acceptable vehicles and solvents that can be employed are water and Ringer's solution, an isotonic sodium chloride. In addition, sterile fixed oils can conventionally be employed as a solvent or suspending medium. For this purpose any bland fixed oil can be employed including synthetic mono- or diglycerides. In addition, fatty acids such as oleic acid can likewise be used in the preparation of injectables. These solutions are sterile and generally free of undesirable matter. These formulations may be sterilized by conventional, well known sterilization techniques. The formulations may contain pharmaceutically acceptable auxiliary substances as required to approximate physiological conditions such as pH adjusting and buffering agents, toxicity adjusting agents, e.g., sodium acetate, sodium chloride, potassium chloride, calcium chloride, sodium lactate and the like. The concentration of GR antagonist in these formulations can vary widely, and will be selected primarily based on fluid volumes, viscosities, body weight, and the like, in accordance with the particular mode of administration selected and the patient's needs. For IV administration, the formulation can be a sterile injectable preparation, such as a sterile injectable aqueous or oleaginous suspension. This suspension can be formulated according to the known art using those suitable dispersing or wetting agents and suspending agents. The sterile injectable preparation can also be a sterile injectable solution or suspension in a nontoxic parenterally-acceptable diluent or solvent, such as a solution of 1,3-butanediol.

In another embodiment, the GR antagonist formulations of the invention can be delivered by the use of liposomes which fuse with the cellular membrane or are endocytosed, i.e., by employing ligands attached to the liposome, or attached directly to the oligonucleotide, that bind to surface membrane protein receptors of the cell resulting in endocytosis. By using liposomes, particularly where the liposome surface carries ligands specific for target cells, or are otherwise preferentially directed to a specific organ, one can focus the delivery of the GR antagonist into the target cells in vivo. (See, e.g., Al-Muhammed, *J. Microencapsul.* 13:293–306, 1996; Chonn, *Curr. Opin. Biotechnol.* 6:698–708, 1995; Ostro, *Am. J. Hosp. Pharm.* 46:1576–1587, 1989).

b. Determining Dosing Regimens for Glucocorticoid Receptor Antagonists

The methods of this invention inhibit or reverse AP-induced weight gain. The amount of GR antagonist adequate to accomplish this is defined as a "therapeutically effective dose". The dosage schedule and amounts effective for this use, i.e., the "dosing regimen," will depend upon a variety of factors, including the type of the AP medication the patient is using, the amount of AP-induced weight gain that has already occurred, the patient's physical status, age and the like. In calculating the dosage regimen for a patient, the mode of administration also is taken into consideration.

The dosage regimen also takes into consideration pharmacokinetics parameters well known in the art, i.e., the GR antagonists' rate of absorption, bioavailability, metabolism, clearance, and the like (see, e.g., Hidalgo-Aragones, *J. Steroid Biochem. Mol. Biol.* 58:611–617, 1996; Groning, *Pharmazie* 51:337–341, 1996; Fotherby, *Contraception* 54:59–69, 1996; Johnson, *J. Pharm. Sci.* 84:1144–1146, 1995; Rohatagi, *Pharmazie* 50:610–613, 1995; Brophy, *Eur. J. Clin. Pharmacol.* 24:103–108, 1983; the latest Remington's, supra). For example, in one study, less than 0.5% of the daily dose of mifepristone was excreted in the urine; the drug bound extensively to circulating albumin (see Kawai, supra, 1989). The state of the art allows the clinician to determine the dosage regimen for each individual patient, GR antagonist and disease or condition treated. As an illustrative example, the guidelines provided below for mifepristone can be used as guidance to determine the dosage regiment, i.e., dose schedule and dosage levels, of any GR antagonist administered when practicing the methods of the invention.

Single or multiple administrations of GR antagonist formulations can be administered depending on the dosage and frequency as required and tolerated by the patient. The formulations should provide a sufficient quantity of active agent, i.e., mifepristone, to effectively inhibit or reverse the weight gain induced by AP medicatioins. For example, a typical preferred pharmaceutical formulation for oral administration of mifepristone would be about 5 to 15 mg/kg of body weight per patient per day, more preferably between about 8 to about 12 mg/kg of body weight per patient per day, most preferably 10 mg/kg of body weight per patient per day, although dosages of between about 0.5 to about 25 mg/kg of body weight per day may be used in the practice of the invention. Lower dosages can be used, particularly when the drug is administered to an anatomically secluded site, such as the cerebral spinal fluid (CSF) space, in contrast to administration orally, into the blood stream, into a body cavity or into a lumen of an organ. Substantially higher dosages can be used in topical administration. Actual methods for preparing parenterally administrable GR antagonist formulations will be known or apparent to those skilled in the art and are described in more detail in such publications as Remington's, supra. See also Nieman, In "Receptor Mediated Antisteroid Action," Agarwal, et al., eds., De Gruyter, New York, 1987.

After a pharmaceutical comprising a GR antagonist of the invention has been formulated in a acceptable carrier, it can be placed in an appropriate container and labeled for treatment of an indicated condition. For administration of GR antagonists, such labeling would include, e.g., instructions concerning the amount, frequency and method of administration. In one embodiment, the invention provides for a kit for inhibiting or reversing AP-induced weight gain in a human which includes a GR antagonist and instructional material teaching the indications, dosage and schedule of administration of the GR antagonist.

EXAMPLES

The following examples are offered to illustrate, but not to limit the claimed invention.

Example 1

Inhibiting or Reversing AP-Induced Weight Gain with Mifepristone

The following example demonstrates how to practice the methods of the invention.

Patient Selection

Individuals who are to begin long term AP administration, or have been under long term AP administration and have gained substantial amount of weight as a result. The patient typically has normal levels of cortisol for his or her age.

Dosage Regimen and Administration of Mifepristone

The glucocorticoid receptor (GR) antagonist, mifepristone, is used in this study. It is administered in dosages of 200 mg daily. Individuals will be given 200 mg of mifepristone daily for six months and evaluated as described below. Dosages will be adjusted if necessary and further evaluations will be performed periodically throughout treatment.

Mifepristone tablets are available from commercial sources such as Shanghai HuaLian Pharmaceuticals Co., Ltd., Shanghai, China.

Assessing Prevention of Weight Gain

To delineate and assess the effectiveness of mifepristone in inhibiting or reversing AP-induced weight gain, the patients' body weight is determined by physical examinations and recorded every two weeks.

Example 2

Measuring Cortisol Levels

To measure cortisol levels of the patients of Example 1, afternoon Cortisol Test measurements are taken and used as the baseline cortisol measure. Cortisol levels are taken at Day 0, at two weeks after receiving the medication (Day 14), and each visit for up to six months and periodically thereafter.

The "Double Antibody Cortisol Kit" (Diagnostic Products Corporation, Los Angeles, Calif.) is used to measure blood cortisol levels. This test is a competitive radioimmunoassay in which $^{125}$I-labeled cortisol competes with cortisol from an clinical sample for antibody sites, and is performed essentially according to manufacturer's instructions using reagents supplied by manufacturer. Briefly, blood is collected by venipuncture and serum separated from the cells. The samples are stored at 2 to 8° C. for up to seven days, or up to two month frozen at −20° C. Before the assay, samples are allowed to come up to room temperature (15–28° C.) by gentle swirling or inversion. Sixteen tubes in duplicate at 25 microliters of serum per tube are prepared. Cortisol concentrations are calculated from the prepared calibration tubes. Net counts equal the average CPM minus the average non-specific CPM. Cortisol concentrations for the unknowns are estimated by interpolation from the calibration curve (Dudley et al., *Clin. Chem.* 31: 1264–1271, 1985).

It is understood that the examples and embodiments described herein are for illustrative purposes only and that various modifications or changes in light thereof will be suggested to persons skilled in the art and are to be included within the spirit and purview of this application and scope of the claims.

What is claimed is:

1. A method of inhibiting or reversing weight gain in a patient being treated with an antipsychotic medication, the method comprising the step of administering to a patient being treated with an antipsychotic medication an amount of a glucocorticoid receptor antagonist effective to inhibit or reverse weight gain, with the proviso that the patient be not otherwise in need of treatment with a glucocorticoid receptor antagonist and that the patient be not suffering from psychotic major depression.

2. The method of claim 1, wherein the patient is being treated with an atypical antipsychotic medication.

3. The method of claim 1, wherein the patient is being treated with an antipsychotic medication selected from the group consisting of clozapine, olanzapine, risperidone, quetiapine, and sertindole.

4. The method of claim 1, wherein the patient has gained at least 2 kg of weight over a ten-week period of treatment with the antipsychotic medication.

5. The method of claim 1, wherein the patient is at least 20% above the healthful weight range.

6. The method of claim 1, wherein the glucocorticoid receptor antagonist comprises a steroidal skeleton with at least one phenyl-containing moiety in the 11-beta position of the steroidal skeleton.

7. The method of claim 6, wherein the phenyl-containing moiety in the 11-beta position of the steroidal skeleton is a dimethylaminophenyl moiety.

8. The method of claim 7, wherein the glucocorticoid receptor antagonist comprises mifepristone.

9. The method of claim 7, wherein the glucocorticoid receptor antagonist is selected from the group consisting of RU009 and RU044.

10. The method of claim 1, wherein the glucocorticoid receptor antagonist is administered in a daily amount of between about 0.5 to about 20 mg per kilogram of body weight per day.

11. The method of claim 10, wherein the glucocorticoid receptor antagonist is administered in a daily amount of between about 1 to about 10 mg per kilogram of body weight per day.

12. The method of claim 11, wherein the glucocorticoid receptor antagonist is administered in a daily amount of between about 1 to about 4 mg per kilogram of body weight per day.

13. The method of claim 1, wherein the administration is once per day.

14. The method of claim 1, wherein the mode of administration is oral.

15. The method of claim 1, wherein the mode of administration is by a transdermal application, by a nebulized suspension, or by an aerosol spray.

* * * * *